United States Patent
Seligman et al.

(10) Patent No.: US 6,752,775 B2
(45) Date of Patent: Jun. 22, 2004

(54) BRACE HINGE WITH TELESCOPING CONDYLE PAD

(75) Inventors: Scott Seligman, Carlsbad, CA (US); Emee Villegas, Oceanside, CA (US)

(73) Assignee: dj Orthopedics, LLC, Vista, CA (US)

( * ) Notice: Subject to any disclaimer, the term of this patent is extended or adjusted under 35 U.S.C. 154(b) by 0 days.

(21) Appl. No.: 10/074,520

(22) Filed: Feb. 11, 2002

(65) Prior Publication Data

US 2003/0153856 A1 Aug. 14, 2003

(51) Int. Cl.$^7$ .................................................. A61F 5/00
(52) U.S. Cl. .................................. 602/16; 602/26
(58) Field of Search .............................. 602/5, 16, 23, 602/26; 128/882

(56) References Cited

U.S. PATENT DOCUMENTS

| | | | |
|---|---|---|---|
| 575,199 A | | 1/1897 | Autenrieth |
| 2,467,907 A | | 4/1949 | Peckham |
| 3,669,105 A | * | 6/1972 | Castiglia ........................ 2/22 |
| 4,136,404 A | | 1/1979 | Lange |
| 4,428,369 A | | 1/1984 | Peckham et al. |
| 4,554,913 A | | 11/1985 | Womack et al. |
| 4,620,532 A | | 11/1986 | Houswerth |
| 4,697,583 A | * | 10/1987 | Mason et al. ................ 602/26 |
| 4,803,975 A | * | 2/1989 | Meyers ........................ 2/22 |
| 4,854,308 A | | 8/1989 | Drillio |
| 4,940,045 A | | 7/1990 | Cromartie |
| 5,018,514 A | * | 5/1991 | Grood et al. ................. 602/16 |
| 5,042,464 A | | 8/1991 | Skwor et al. |
| 5,063,917 A | * | 11/1991 | Young et al. ................ 602/26 |
| 5,086,760 A | | 2/1992 | Neumann et al. |
| 5,176,623 A | | 1/1993 | Stetman et al. |
| 5,316,547 A | | 5/1994 | Gildersleeve |
| 5,360,394 A | | 11/1994 | Christensen |
| 5,415,625 A | | 5/1995 | Cassford et al. |
| 5,458,565 A | | 10/1995 | Tillinghast, III et al. |
| 5,520,622 A | | 5/1996 | Bastyr et al. |
| 5,527,268 A | | 6/1996 | Gildersleeve et al. |
| 5,542,911 A | | 8/1996 | Cassford et al. |
| 5,586,970 A | | 12/1996 | Morris et al. |
| 5,658,244 A | * | 8/1997 | Townsend et al. ............ 602/26 |
| 5,674,188 A | * | 10/1997 | Young ........................ 602/16 |
| 5,743,865 A | | 4/1998 | Townsend |
| 5,772,618 A | * | 6/1998 | Mason et al. ................ 602/16 |
| 5,807,294 A | * | 9/1998 | Cawley et al. ................ 602/26 |
| 5,857,989 A | * | 1/1999 | Smith, III ................... 602/16 |
| 6,039,709 A | * | 3/2000 | Bzoch ........................ 602/16 |
| 6,110,138 A | * | 8/2000 | Shirley ....................... 602/16 |
| 6,413,232 B1 | * | 7/2002 | Townsend et al. ............ 602/16 |
| 6,527,733 B1 | * | 3/2003 | Ceriani et al. ................ 602/16 |

FOREIGN PATENT DOCUMENTS

GB     2 327 044      1/1999

\* cited by examiner

*Primary Examiner*—Michael A. Brown
*Assistant Examiner*—Fenn C Mathew
(74) *Attorney, Agent, or Firm*—Knobbe, Martens, Olson & Bear LLP (57) ABSTRACT

A brace hinge is provided having an adjustable pressure-applying assembly mounted to an inside of the hinge. A brace including the hinge can apply pressure to a joint in a medial or lateral direction. The hinge includes anterior and posterior apertures containing anterior and posterior adjustment members that control a position and orientation of the pressure-applying assembly relative to the hinge. Through selective adjustment of the adjustment members, the hinge can apply greater pressure to an anterior portion of the joint than to a posterior portion of the joint, and vice versa. A method of treating a joint using a brace including such a hinge is also provided.

34 Claims, 9 Drawing Sheets

BRACE HINGE WITH TELESCOPING CONDYLE PAD

BACKGROUND OF THE INVENTION

1. Field of the Invention

The present invention relates to orthopedic braces. More particularly, the present application describes a hinge for an orthopedic brace having a condyle pad that is adjustable toward and away from a joint.

2. Description of the Related Art

Orthopedic knee braces are typically worn either to support a healthy knee joint and prevent injury, or to stabilize a knee joint that has been destabilized by an injury or other condition. These braces generally include rigid structural components that support or stabilize the knee joint. The rigid structural components are dynamically linked together by one or more hinges that enable controlled pivotal movement of the knee joint during user activity or rehabilitative therapy. The brace is positioned on the leg such that the hinges traverse the knee joint, while the rigid components are secured to the leg above and below the knee joint.

Osteoarthritis is a degenerative disease that destabilizes the knee joint. The disease commonly results from aging, knee joint overuse, or injury. A person afflicted with osteoarthritis suffers chronic pain when his or her knee joint is statically or dynamically loaded. The pain is caused by an unbalanced loading on the knee joint. The unbalanced loading often closes a compartment between the condyles of the femur and tibia. When these condyles contact one another, their contacting surfaces develop painful abrasions.

Wearing an orthopedic knee brace on the affected leg is one common noninvasive method of treating osteoarthritis pain. These braces apply a force to a medial or lateral side of the knee in order to unload the affected compartment of the knee joint and eliminate contact between the femur and tibia. U.S. Pat. No. 5,277,698 discloses an example of such a brace. This brace applies a force to the knee on that side of the knee remote from the compartment having osteoarthritis as the knee moves to extension. Preferably, the force is applied at a point about 10° to 15° posterior of the normal axis of rotation of the knee.

U.S. Pat. No. 5,586,970 discloses a knee brace having a medial condylar pad 34 and a lateral condylar pad 36 that are each independently adjustable in side-to-side motion. This independent adjustment permits either medial condylar pad 34 or lateral condylar pad 36 to have variable pressure with respect to a user's knee 26.

U.S. Pat. No. 5,807,294 discloses a hinge assembly 14 for an orthopedic knee brace 10 that pivotally couples an upper arm 34 and a lower arm 46. The hinge assembly includes a pad assembly 24, 26, a hinge 22, and upper and lower adjustment members 74, 88 enabling adjustment of the normal force applied by the hinge assembly to the knee joint for the treatment of osteoarthritis. The hinge includes an end of the upper arm, an end of the lower arm, outer and inner hinge plates 58, 60 positioned on opposite sides of the ends, and upper and lower hinge fasteners 68, 82. The upper and lower hinge fasteners each have a bore therethrough that is internally threaded. The upper hinge fastener rotatably connects the end of the upper arm to the outer and inner hinge plates and the lower hinge fastener rotatably connects the end of the lower arm to the outer and inner hinge plates. The upper adjustment member has external threads that are received by the internal threads of the upper hinge fastener to telescopically couple the upper adjustment member to the upper hinge fastener. The lower adjustment member likewise has external threads that are received by the internal threads of the lower hinge fastener to telescopically couple the lower adjustment member to the lower hinge fastener. Both the upper and lower adjustment members have ends that are substantially fixedly coupled to the pad holder. As a result, the pad assembly is selectively displaceable toward or away from the hinge when the user selectively displaces the upper and lower adjustment members through the upper and lower bores of the upper and lower hinge fasteners.

No current brace allows a wearer to provide greater pressure on an anterior portion of his or her knee as compared to a posterior portion. Such a brace would be advantageous for both treating and preventing certain types of injuries.

SUMMARY OF THE INVENTION

The preferred embodiments of the brace hinge with telescoping condyle pad have several features, no single one of which is solely responsible for their desirable attributes. Without limiting the scope of this brace hinge with telescoping condyle pad as expressed by the claims that follow, its more prominent features will now be discussed briefly. After considering this discussion, and particularly after reading the section entitled "Detailed Description of the Preferred Embodiments," one will understand how the features of the preferred embodiments provide advantages, which include the capability to apply greater pressure to an anterior portion of a joint than to a posterior portion of the joint, and vice versa.

A preferred embodiment of the brace hinge comprises a first hinge plate including an anterior aperture and a posterior aperture. A lateral/medial force application assembly is attached to the first hinge plate by an anterior adjustment member and a posterior adjustment member. The adjustment members are connected at a medial end of each to the force application assembly, and the anterior adjustment member telescopingly engages the anterior aperture and the posterior adjustment member telescopingly engages the posterior aperture, such that manipulation of the adjustment members enables adjustment of a distance between the first hinge plate and the force application assembly.

Another preferred embodiment comprises a method of treating a knee. The method comprises the steps of applying a brace to a leg including the knee, and applying pressure to a medial or lateral side of the knee. The pressure is applied to the knee such that an anterior portion of the knee is under greater pressure than a posterior portion of the knee, or vice versa.

BRIEF DESCRIPTION OF THE DRAWINGS

The preferred embodiments of the brace hinge with telescoping condyle pad, illustrating its features, will now be discussed in detail. These embodiments depict the novel and non-obvious brace hinge with telescoping condyle pad shown in the accompanying drawings, which are for illustrative purposes only. These drawings include the following figures, in which like numerals indicate like parts.

DETAILED DESCRIPTION OF THE PREFERRED EMBODIMENTS

Figure 1:
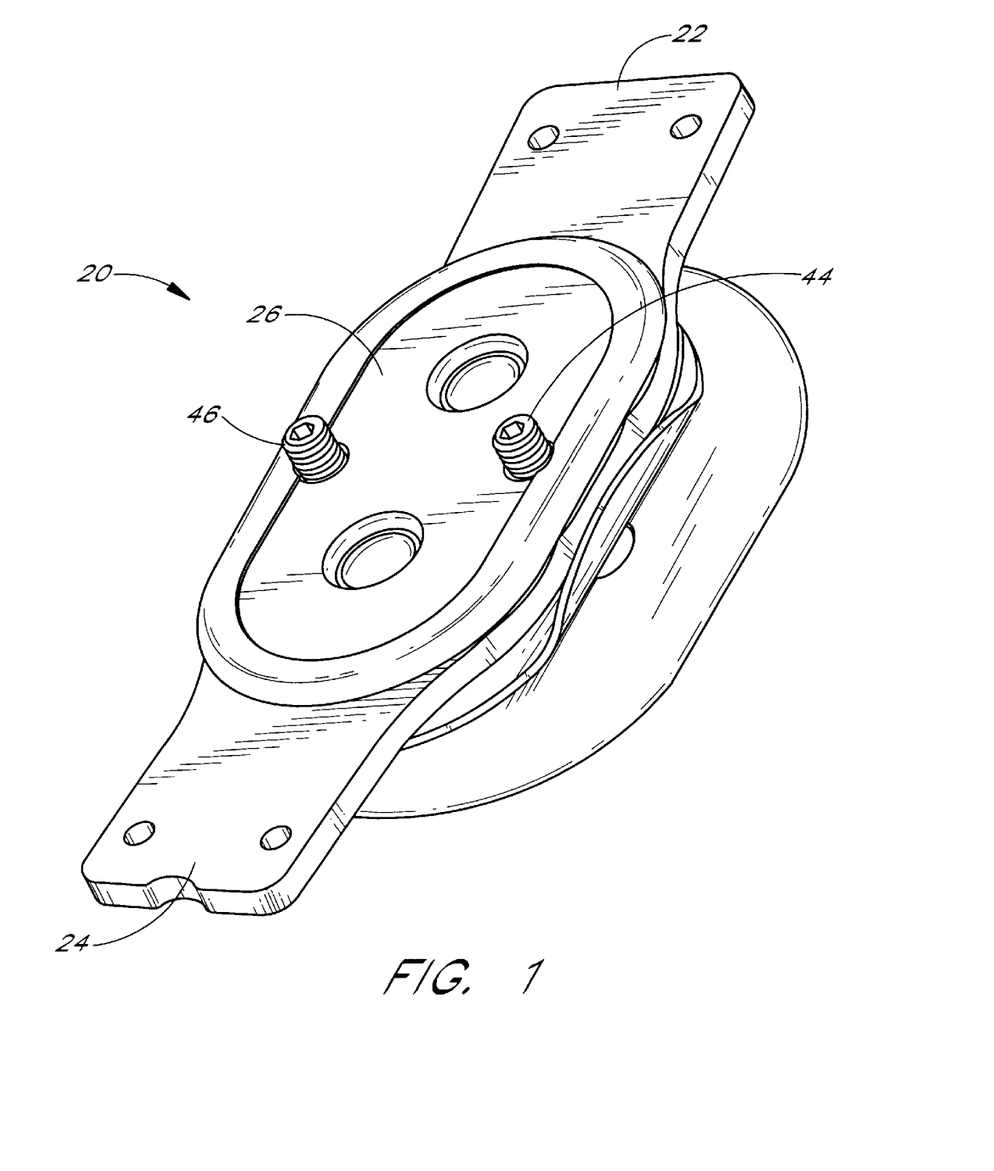
FIG. 1 is a perspective view of a preferred embodiment of the hinge with telescoping condyle pad according to the present invention.

FIG. 1 illustrates a preferred embodiment of the brace hinge with telescoping condyle pad. The hinge 20 is preferably a component of a knee brace (not shown) that is designed to treat osteoarthritis. Those of skill in the art will appreciate, however, that the hinge 20 is adapted for use in a variety of braces, including prophylactic knee braces worn about healthy knees, and braces for parts of the body other than the knee. For simplicity, the construction and function of the hinge 20 will be described with reference to a knee brace.

The illustrated hinge 20 is adapted for use on a lateral side of a right leg, or a medial side of a left leg. Those of skill in the art will appreciate that a substantially identical hinge having a mirror image configuration would be adapted for use on a medial side of a right leg, or a lateral side of a left leg. For simplicity, the present hinge 20 will be described with reference to a lateral side of a right leg. The scope of the present hinge 20 is not, however, limited to an application to a lateral side of a right leg.

Figure 2:
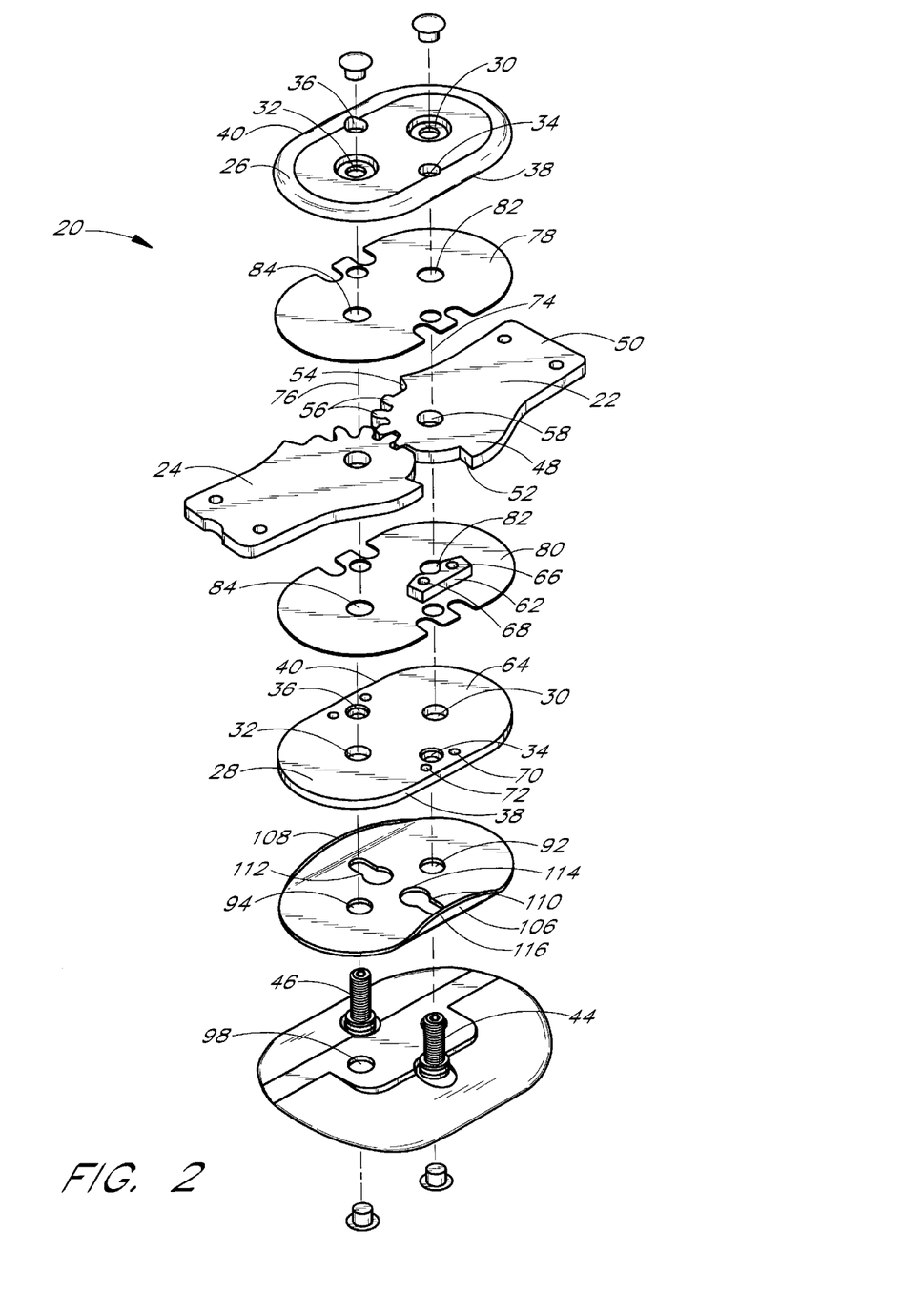
FIG. 2 is an exploded perspective view of the hinge of FIG. 1.
Figure 3:
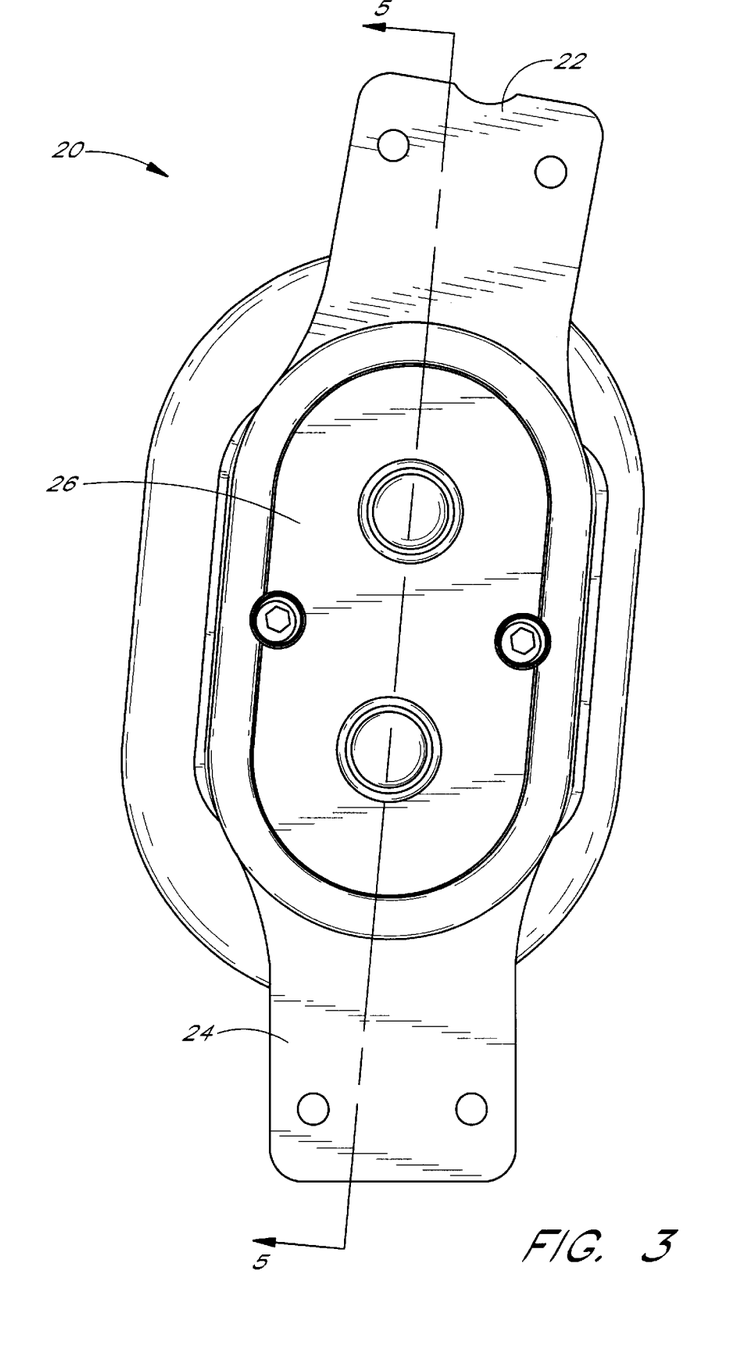
FIG. 3 is a front elevation view of the hinge of FIG. 1.
Figure 4:
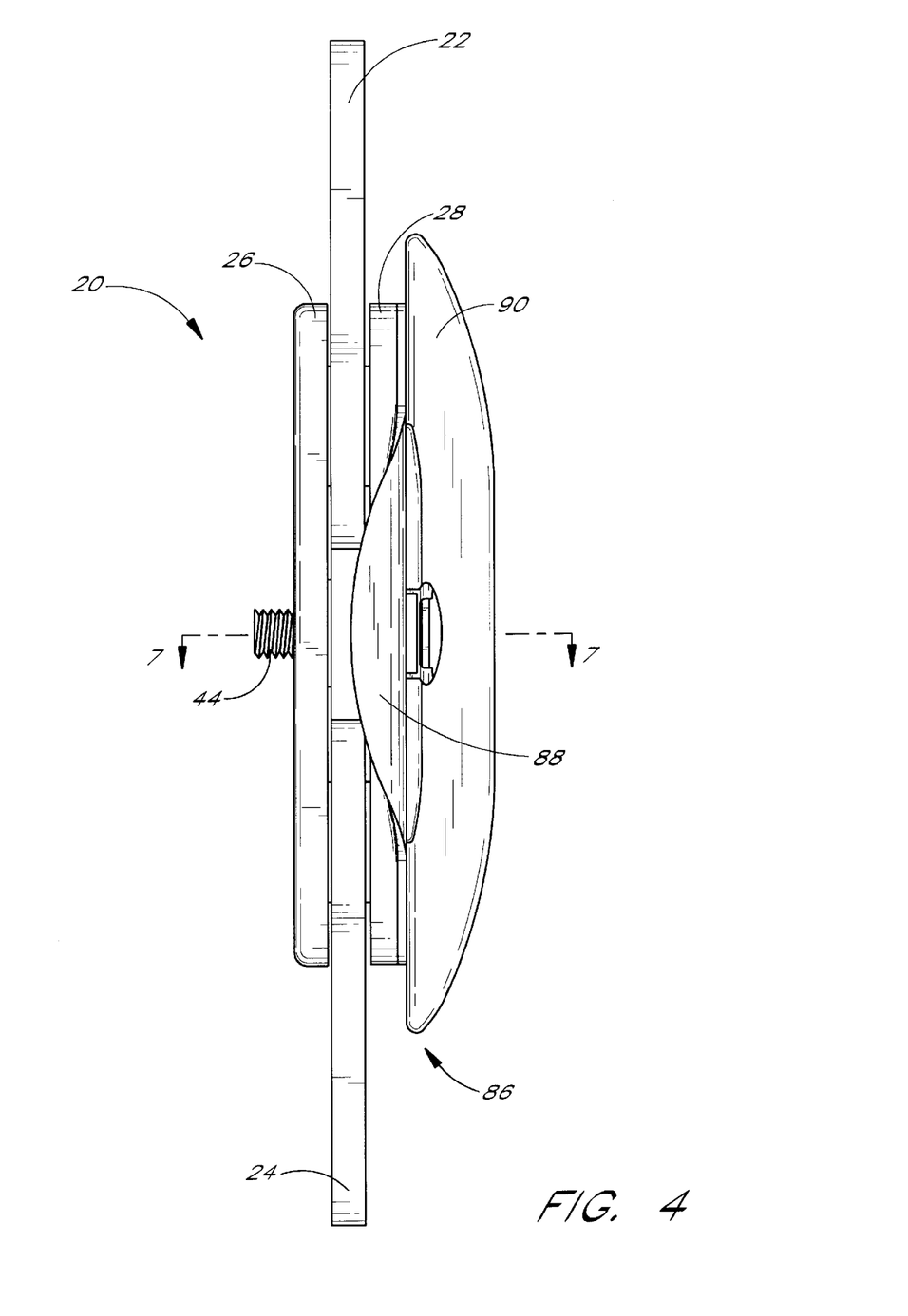
FIG. 4 is a right-side elevation view of the hinge of FIG. 1.

The hinge 20 comprises a proximal arm 22 and a distal arm 24 pivotably engaging a hinge assembly. The hinge assembly comprises a lateral hinge plate 26 and a medial hinge plate 28, as shown in the exploded view of FIG. 2. Each of the hinge plates 26, 28 is substantially oval in front elevation aspect (FIG. 3), and each includes a proximal aperture 30 and a distal aperture 32 (FIG. 2). The proximal aperture 30 is located substantially in the center of a proximal half of each hinge plate 26, 28, and the distal aperture 32 is located substantially in the center of a distal half of each hinge plate 26, 28.

Each of the hinge plates 26, 28 also includes an anterior aperture 34 and a posterior aperture 36. Each anterior aperture 34 is located near a center of an anterior edge 38 of its respective plate, and each posterior aperture 36 is located near a center of a posterior edge 40 of its respective plate. Those of skill in the art will appreciate that the apertures 34, 36 need not be arranged in the fashion illustrated. Both could for example, be located toward one side of the hinge plates, or be spaced from a proximal/distal axis of the hinge plates. The anterior and posterior apertures 34, 36 include internal threads that cooperate with an anterior loading screw 44 and a posterior loading screw 46, respectively, to adjust an amount of pressure exerted on a lateral side of the wearer's knee, as explained below.

The proximal arm 22 is a substantially flat plate having a hinge-engaging portion 48 at a distal end, and an upright-engaging portion 50 at a proximal end. The upright-engaging portion 50 is substantially rectangular, while the hinge-engaging portion 48 has a complex perimeter, including an anterior shoulder 52, a posterior shoulder 54, and a plurality of gear teeth 56 along proximal and posterior edges. The proximal arm 22 includes a pivot aperture 58 near the distal end. The distal arm 24 is substantially identical to the proximal arm 22, but is a substantial mirror image of the proximal arm 22 about a line that passes through a center of the hinge 20 in an anterior/posterior direction.

In a knee brace, the proximal arm 22 preferably engages a rigid proximal upright (not shown), and the distal arm 24 preferably engages a rigid distal upright (not shown). The proximal and distal uprights are secured to the wearer's thigh and calf, respectively, with straps, cuffs or other suitable attachment devices. The uprights and their attachment devices thus anchor the brace to the wearer's leg and enable the brace to provide the advantages outlined below.

Figure 5:
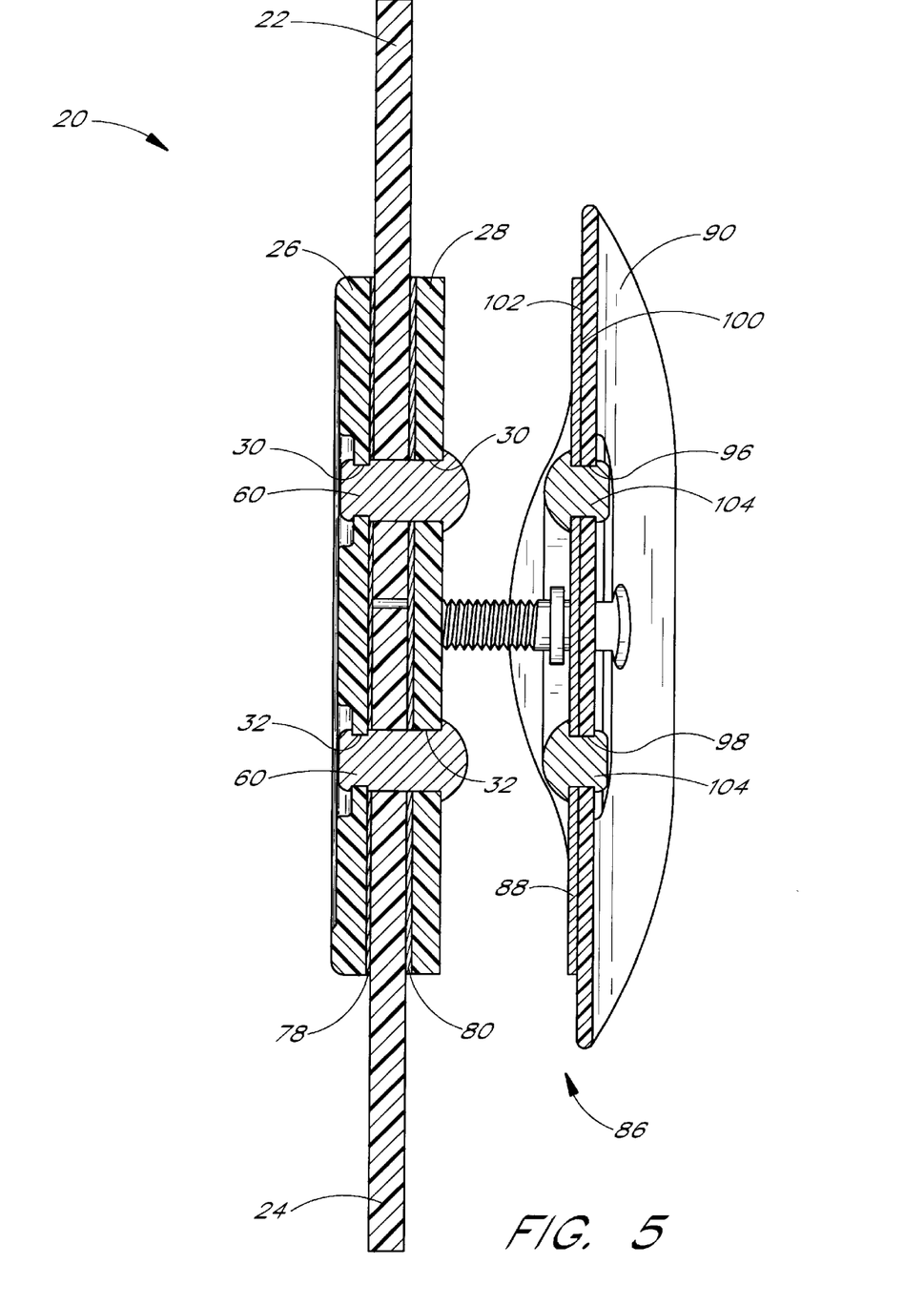
FIG. 5 is a right-side section view of the hinge of FIG. 1 taken along the line 5—5 of FIG. 3.

The proximal and distal arms 22, 24 are sandwiched between the lateral and distal hinge plates 26, 28 such that the pivot aperture 58 on the proximal arm 22 is coaxial with the proximal apertures 30 of the hinge plates 26, 28, and the pivot aperture on the distal arm 24 is coaxial with the distal apertures 32 of the hinge plates 26, 28. The arms 22, 24 are preferably attached to the hinge plates 26, 28 with rivets or other suitable attachment members that allow the arms to pivot with respect to the hinge plates 26, 28. In the embodiment of FIG. 5, a pair of lateral rivets 60 pass through the proximal and distal apertures 30, 32 of the lateral hinge plate 26, through the pivot apertures of the proximal and distal arms 22, 24, and through the proximal and distal apertures 30, 32 of the medial hinge plate 28. Those of skill in the art will appreciate that other attachment devices and methods could be used instead of the attachment configuration shown.

An optional extension stop 62 (FIG. 2) is mounted to a lateral face 64 of the medial hinge plate 28 near a center of the anterior edge 38. The anterior shoulder 52 of each arm 22, 24 cooperates with the extension stop 62 to define a maximum extension angle for each arm 22, 24. An optional flexion stop (not shown) is securable to the medial hinge plate 28 near a center of the posterior edge 40. The posterior shoulder 54 of each arm cooperates with the flexion stop to define a maximum flexion angle for each arm 22, 24.

In the illustrated embodiment, the extension stop 62 includes proximal and distal apertures 66, 68 that align with corresponding apertures 70, 72 adjacent the anterior edge 38 of the medial hinge plate 28. The extension stop 62 is secured to the medial hinge plate 28 with threaded fasteners, rivets, or other suitable attachment members that cooperate with the apertures 66, 68, 70, 72. The optional flexion stop, if one is provided, is secured to the medial hinge plate 28 in a similar fashion. Those of skill in the art will appreciate that the stops could be secured to the hinge plates 26, 28 in a variety of alternate ways, such as with an adhesive. Those of skill in the art will further appreciate that neither the extension stop 62 nor the flexion stop is essential to achieving the advantages of the hinge 20.

As illustrated in FIG. 2, an axis of rotation 74 of the proximal arm 22 is parallel to, but spaced from, an axis of rotation 76 of the distal arm 24. Such a bicentric hinge assembly more closely approximates the bending dynamics of the human knee, as is well understood in the art of orthopedic bracing. Those of skill in the art will appreciate, however, that the features and advantages of the present hinge 20 may also be achieved with a monocentric hinge.

Preferably, a lateral spacer 78 separates the lateral hinge plate 26 from the arms 22, 24, and a medial spacer 80 separates the medial hinge plate 28 from the arms 22, 24. Each of the spacers 78, 80 is shaped substantially the same as the hinge plates 26, 28, including a substantially oval-shaped perimeter and proximal and distal apertures 82, 84. The spacers 78, 80 are oriented such that their proximal and distal apertures 82, 84 align with the proximal and distal apertures 30, 32, respectively, of the hinge plates 26, 28. The spacers 78, 80 are preferably constructed of a material having a low coefficient of friction, such as a plastic. The spacers 78, 80 thus enable the arms 22, 24 to rotate more easily within the hinge assembly. Those of skill in the art will appreciate that the spacers 78, 80 could be shaped much differently, or could be eliminated entirely, without departing from the spirit of the hinge 20.

A lateral/medial force application assembly 86 telescopingly engages the hinge assembly on a medial side, as shown in FIGS. 4, 5 and 7A–7C. The assembly comprises a rigid loading plate 88 and a substantially rigid condyle shell 90. For comfort, a resilient pad (not shown) may be attached to a medial surface of the shell 90. Either the shell 90 or the optional pad applies selective pressure to the lateral side of the wearer's right knee in a manner described below.

The loading plate 88 is substantially oval shaped and includes a proximal aperture 92 (FIGS. 2 and 7A) and a distal aperture 94 corresponding to the proximal and distal apertures 30, 32, respectively, of the hinge plates 26, 28. The condyle shell 90 is also substantially oval shaped and includes proximal and distal apertures 96, 98 (FIGS. 2 and 5) corresponding to the proximal and distal apertures 30, 32, respectively, of the loading plate 88. A medial surface 100 of the loading plate 88 is secured to a lateral surface 102 of the condyle shell 90, as shown in FIG. 5. In the illustrated embodiment, the loading plate 88 is secured to the condyle shell 90 via a pair of medial rivets 104 that cooperate with the proximal and distal apertures 92, 94, 96, 98 on the loading plate 88 and condyle shell 90. Those of skill in the art will appreciate that the loading plate 88 and the condyle shell 90 could be secured to one another by other appropriate methods, such as by an adhesive.

Adjustment of the loading plate 88 and condyle shell 90 provides selective pressure on the wearer's knee, as described below. Thus, the loading plate 88 is preferably constructed of a rigid material such as a metal. In the illustrated embodiment, anterior and posterior edges 106, 108 (FIGS. 2 and 7A) of the loading plate 88 are bent away from a plane of the plate 88 in a lateral direction. The bent edges 106, 108 increase the bending strength of the plate 88, enhancing the ability of the plate 88 to apply pressure to the wearer's knee. Those of skill in the art will appreciate that the bent edges 106, 108 are not necessary to achieve the advantages of the hinge 20.

The loading plate 88 includes an anterior slot 110 (FIGS. 2 and 7A) running in an anterior/posterior direction. The anterior slot 110 is located near a center of the loading plate 88 as measured in a proximal/distal direction. The anterior slot 110 includes a wide portion at a posterior end 114, and a narrow portion at an anterior end 116. The loading plate 88 also includes a posterior slot 112 that is substantially identical to the anterior slot 110, but is a mirror image of the anterior slot 110 about a line bisecting the loading plate 88 in a proximal/distal direction.

Figure 6:
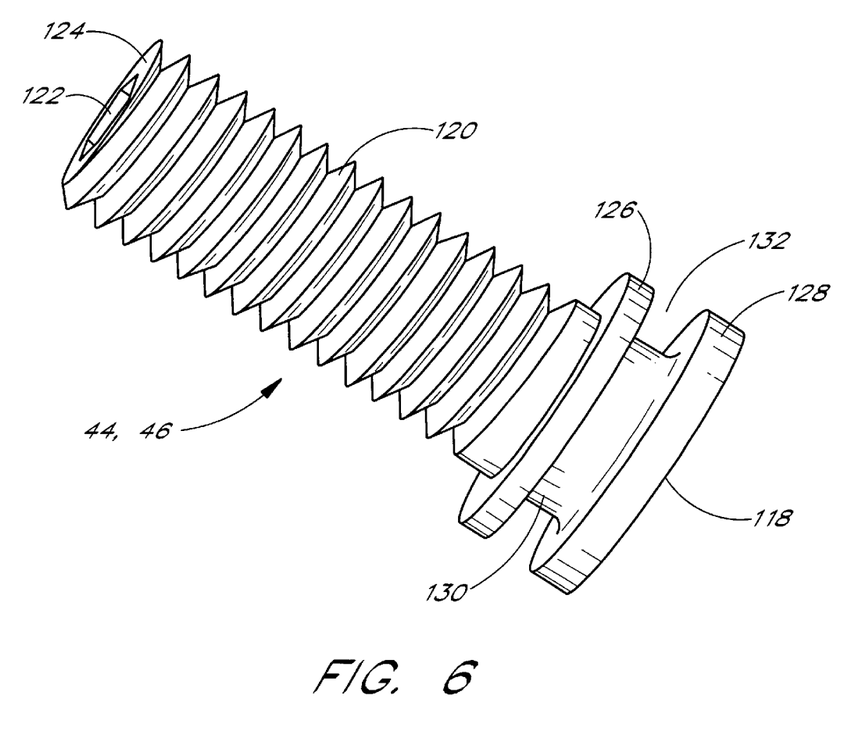
FIG. 6 is a perspective view of a loading screw of the hinge of FIG. 1.
Figure 7A:
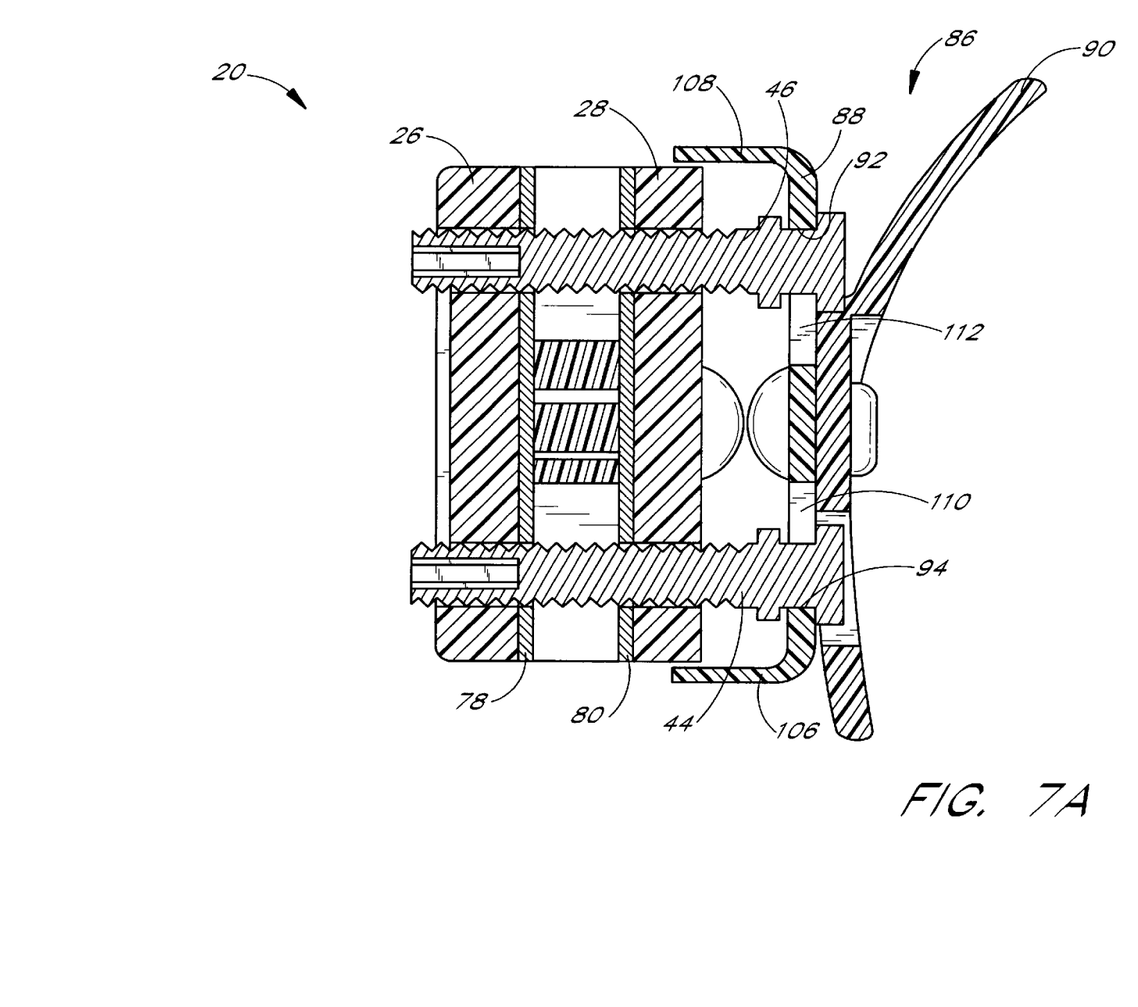
FIG. 7A is a top section view of the hinge of FIG. 1 taken along the line 7—7 of FIG. 4, illustrating the medial/lateral force application assembly at a minimum extension from the hinge.
Figure 7B:
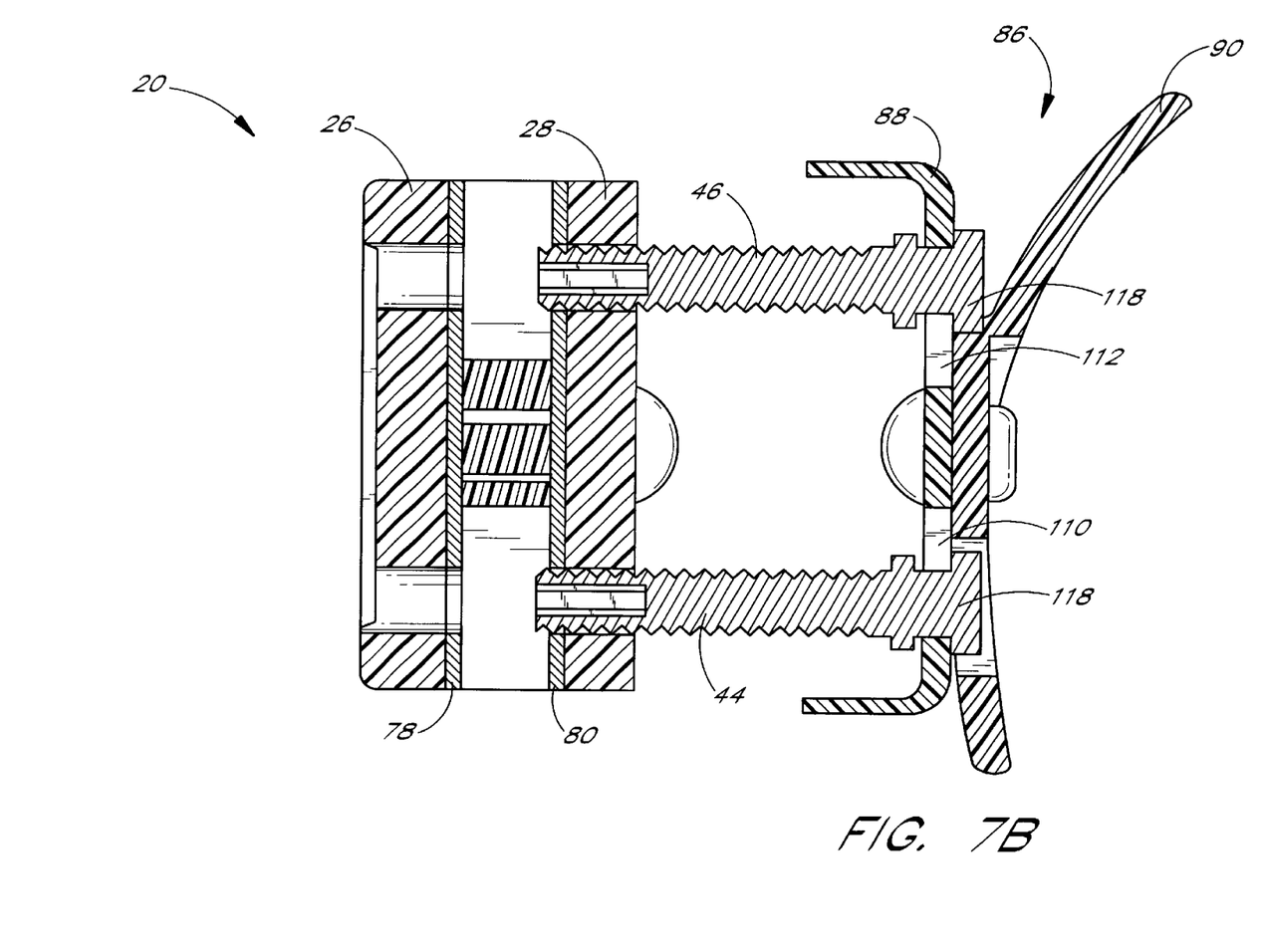
FIG. 7B is a top section view of the hinge of FIG. 1 taken along the line 7—7 of FIG. 4, illustrating the medial/lateral force application assembly at a maximum extension from the hinge.

The anterior slot 110 receives a medial end 118 of an anterior loading screw 44, illustrated in FIGS. 6 and 7B. The posterior slot 112 receives a medial end 118 of a posterior loading screw 46. The anterior and posterior loading screws 44, 46 are substantially identical. As FIG. 6 illustrates, the screws 44, 46 include a threaded lateral portion 120 having a drive tool engagement feature, such as a female hex key 122, on a lateral face 124. The threaded portion 120 terminates near a medial end of the screw 44, 46 in a first coaxial disk 126 having a diameter larger than that of the threaded portion 120. A second coaxial disk 128 is attached to the first disk 126 via a coaxial cylindrical portion 130 having a diameter substantially the same as the threaded portion 120. A space between the two disks 126, 128 thus defines an annular gap 132.

The gap 132 on the anterior loading screw 44 engages the anterior slot 110 on the loading plate 88, and the gap 132 on the posterior loading screw 46 engages the posterior slot 112 on the loading plate 88, as shown in FIG. 7B. The disks 126, 128 at the medial ends 118 of the screws 44, 46 each have a smaller diameter than a width of the wide portions of the anterior and posterior slots 110, 112. However, the disks 126, 128 each have a larger diameter than a width of the narrow portions of the anterior and posterior slots 110, 112. Further, the cylindrical portions 130 of each screw 44, 46 between the disks 126, 128 have a smaller diameter than the width of the narrow portions of the anterior and posterior slots 110, 112. Thus, the anterior loading screw 44 is insertable within the wide portion of the anterior slot 110 and slidable into the narrow portion of the anterior slot 110 such that the sides of the narrow portion of the anterior slot 110 are disposed between the disks 126, 128. The anterior slot 110 thus fixes the anterior loading screw 44 against translation in a direction perpendicular to the loading plate 88. The slot sides are, however, somewhat thinner than the distance between the disks 126, 128, such that there is a small amount of "play" between the loading plate 88 and the screws 44, 46, as shown in FIG. 7B. The posterior loading screw 46 is engageable with the posterior slot 112 in the same manner that the anterior loading screw 44 is engageable with the anterior slot 110.

Figure 7C:
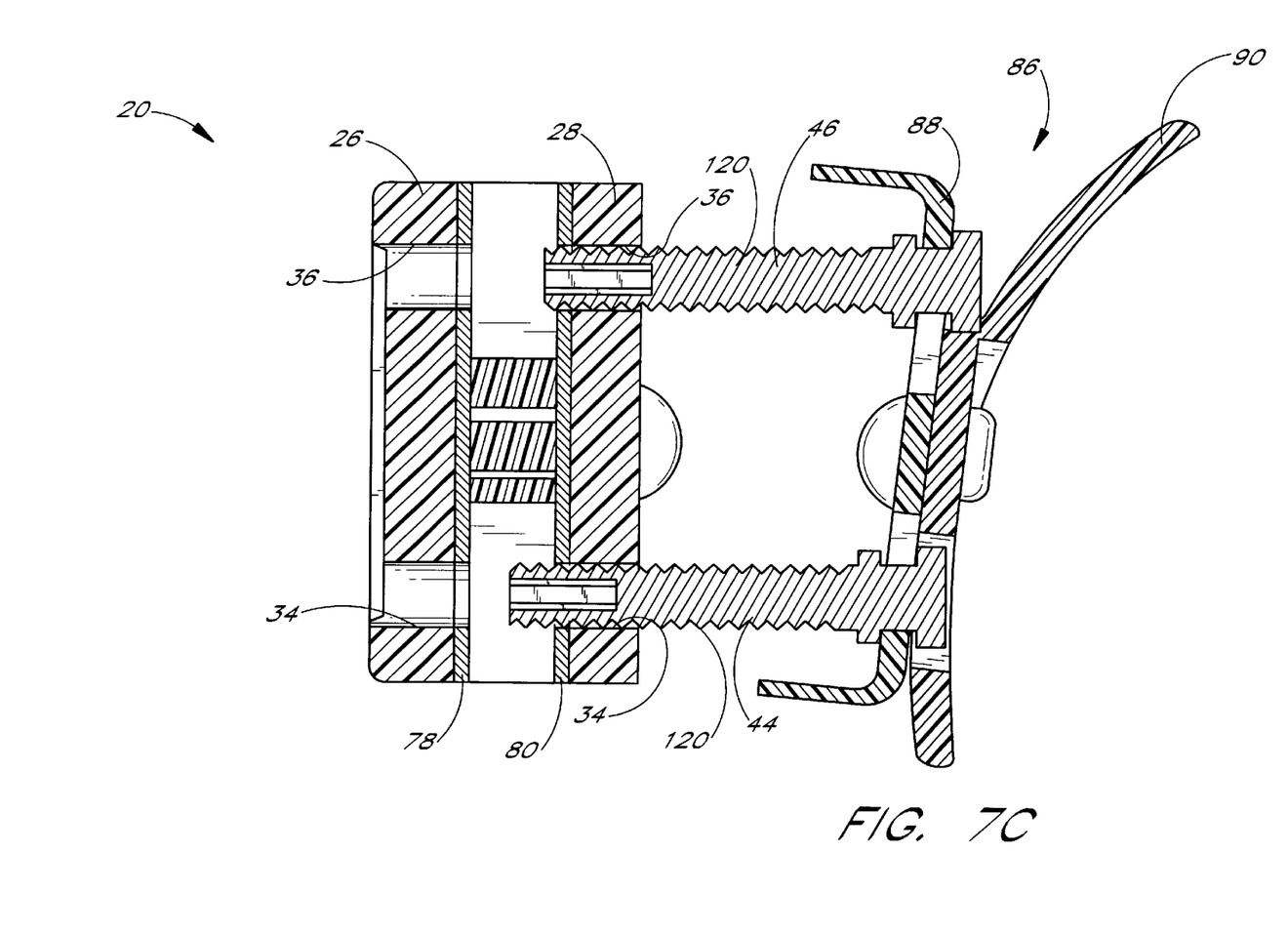
FIG. 7C is a top section view of the hinge of FIG. 1 taken along the line 7—7 of FIG. 4, illustrating the medial/lateral force application assembly in an orientation for applying greater force to a posterior portion than to an anterior portion of a wearer's knee.

The threaded portion 120 of the anterior loading screw 44 engages the anterior holes 34 in the hinge plates 26, 28, as shown in FIG. 7C. The threaded portion 120 of the posterior loading screw 46 engages the posterior holes 36 in the hinge plates 26, 28. Thus, the screws 44, 46 are selectively positionable with respect to the hinge plates 26, 28 in a direction perpendicular to the hinge plates 26, 28. Because the screws 44, 46 are fixed to the loading plate 88, adjusting the position of the screws 44, 46 within the apertures also adjusts the position and orientation of the loading plate 88 and condyle shell 90 with respect to the hinge plates 26, 28.

FIG. 7A illustrates the loading screws 44, 46 adjusted such that both screws 44, 46 extend a minimum distance in the medial direction from the hinge plates 26, 28. In this configuration, the loading plate 88 and condyle shell 90 are substantially parallel to the hinge plates 26, 28 and spaced only slightly from the hinge plates 26, 28. The condyle shell 90 (or optional pad) thus applies little or no pressure to the wearer's knee, and any pressure is applied evenly across the knee in an anterior/posterior direction.

FIG. 7B illustrates the loading screws 44, 46 adjusted such that both screws 44, 46 extend a maximum distance in the medial direction from the hinge plates 26, 28. In this configuration, the loading plate 88 and condyle shell 90 are substantially parallel to the hinge plates 26, 28 and spaced greatly from the hinge plates 26, 28. The condyle shell 90 (or optional pad) thus applies maximum pressure to the wearer's knee, and the pressure is applied evenly across the knee in an anterior/posterior direction.

FIG. 7C illustrates the loading screws 44, 46 adjusted such that the posterior loading screw 46 extends from the hinge plates 26, 28 in the medial direction a greater amount than the anterior loading screw 44. In this configuration, the loading plate 88 and condyle shell 90 are oriented at an angle relative to the hinge plates 26, 28. The condyle shell 90 (or optional pad) thus applies greater pressure to a posterior portion of the wearer's knee than to an anterior portion of the wearer's knee.

Although not depicted, the lateral/medial force application assembly 86 is also configurable in a manner opposite from that of FIG. 7C. In this configuration the anterior loading screw 44 extends from the hinge plates 26, 28 in the medial direction a greater amount than the posterior loading screw 46. The condyle shell 90 (or optional pad) thus applies greater pressure to an anterior portion of the wearer's knee than to a posterior portion of the wearer's knee.

The ability of a brace including the present hinge 20 to apply differing pressures to anterior and posterior portions of a wearer's knee enables such a brace to be adapted to a wide variety of treatment situations. Every human knee is unique, and there are a wide variety of knee injuries and knee injury prevention situations. In certain situations it is advantageous for a patient to have greater pressure applied to an anterior portion of his or her knee, and in certain other situations it is advantageous for a patient to have greater pressure applied to a posterior portion of his or her knee. Current braces do not allow for such adjustable application of pressure to anterior and posterior portions of a patient's knee as does a brace including the present hinge 20.

Further, the configuration of the present hinge 20 spread loads over a greater area of the hinge plates 26, 28 than other current designs. For example, in the hinge of U.S. Pat. No. 5,807,294, described above, the adjustment members 74, 88 pass through the hinge fasteners 68, 82. Thus, all loads applied to the lateral pad 26 are transmitted to the hinge fasteners, and all loads applied to the arms 34, 46 are also transmitted to the hinge fasteners. The hinge fasteners in turn transmit these loads to the areas of the hinge plates 58, 60 in which they are disposed. This configuration concentrates tremendous loads on two small areas of the hinge plates 58, 60. These loads lead to rapid wear of the hinge plates 58, 60 and eventually failure.

In the configuration of the present hinge 20, however, loads applied to the condyle shell 90 are transmitted through the loading screws 44, 46 to the anterior and posterior aperture 34, 36 of the hinge plates 26, 28. Loads applied to the arms 22, 24 are transmitted through the lateral rivets 60 to the proximal and distal aperture 30, 32 of the hinge plates 26, 28. The loads are thus spread over a greater area of the hinge plates 26, 28. The hinge plates 26, 28 are thus able to withstand more prolonged use without failure. Alternatively, the hinge plates 26, 28 are able to be made using less material, which results in lighter hinge plates and an overall lighter brace.

SCOPE OF THE INVENTION

The above presents a description of the best mode contemplated for the present brace hinge with telescoping condyle pad, and of the manner and process of making and using it, in such full, clear, concise, and exact terms as to enable any person skilled in the art to which it pertains to make and use this brace hinge with telescoping condyle pad. This brace hinge with telescoping condyle pad is, however, susceptible to modifications and alternate constructions from that discussed above which are fully equivalent. Consequently, it is not the intention to limit this brace hinge with telescoping condyle pad to the particular embodiments disclosed. On the contrary, the intention is to cover all modifications and alternate constructions coming within the spirit and scope of the brace hinge with telescoping condyle pad as generally expressed by the following claims, which particularly point out and distinctly claim the subject matter of the brace hinge with telescoping condyle pad.

What is claimed is:

1. A brace hinge comprising:
 a first hinge plate including a first aperture defining a first rotation axis of the hinge, an anterior aperture and a posterior aperture, the anterior aperture and the posterior aperture being spaced from the first aperture;
 a lateral/medial force application assembly;
 an anterior adjustment member; and
 a posterior adjustment member; wherein the adjustment members are connected at a first end of each to the force application assembly, and the anterior adjustment member telescopingly engages the anterior aperture and the posterior adjustment member telescopingly engages the posterior aperture, such that manipulation of the adjustment members enables adjustment of a distance between the first hinge plate and the force application assembly.

2. The brace hinge of claim 1, wherein the adjustment members comprise external threads that cooperate with internal threads of the anterior and posterior apertures to define a position of the adjustment members with respect to the hinge plates.

3. The brace hinge of claim 1, wherein manipulation of the adjustment members further enables adjustment of an orientation of the force application assembly with respect to the first hinge plate.

4. The brace hinge of claim 1, further comprising a second hinge plate.

5. The brace hinge of claim 4, wherein the first and second hinge plates each include a proximal aperture and a distal aperture.

6. The brace hinge of claim 1, further comprising a proximal arm and a distal arm pivotably secured between the first and second hinge plates.

7. The brace hinge of claim 6, wherein rivets secure the proximal and distal arms between the first and second hinge plates.

8. The brace hinge of claim 6, further comprising a first spacer separating the first hinge plate from the proximal arm and distal arm.

9. The brace hinge of claim 8, further comprising a second spacer separating the second hinge plate from the proximal arm and distal arm.

10. The brace hinge of claim 6, further comprising an extension limit attached to the second hinge plate and defining a maximum extension angle of the proximal arm and distal arm.

11. The brace hinge of claim 6, further comprising a flexion limit attached to the second hinge plate and defining a maximum flexion angle of the proximal arm and distal arm.

12. The brace hinge of claim 1, wherein the force application assembly comprises a rigid loading plate.

13. The brace hinge of claim 12, wherein the loading plate is secured to the first ends of the adjustment members.

14. The brace hinge of claim 12, wherein the force application assembly further comprises a semi-rigid member secured to the loading plate.

15. The brace hinge of claim 14, wherein the force application assembly further comprises a resilient pad secured to the semi-rigid member.

16. The brace hinge of claim 1, further comprising a second aperture defining a second rotation axis of the hinge.

17. The brace hinge of claim 7, wherein the first and second apertures define a line, and the anterior aperture is located to a first side of the line and the posterior aperture is located to a second side of the line.

18. The brace hinge of claim 1, further comprising a brace.

19. The brace hinge of claim 18, wherein the brace is a knee brace.

20. A brace hinge, comprising:
   a first hinge plate including an anterior aperture and a posterior aperture, the apertures being located such that when a brace incorporating the hinge is properly positioned upon a wearer, the anterior aperture is located towards a front of the wearer, and the posterior aperture is located towards a rear of the wearer;
   a lateral/medial force application assembly;
   an anterior adjustment member; and
   a posterior adjustment member; wherein
   the adjustment members are connected at a first end of each to the force application assembly, and the anterior adjustment member telescopingly engages the anterior aperture and the posterior adjustment member telescopingly engages the posterior aperture, such that manipulation of the adjustment members enables adjustment of a distance between the first hinge plate and the force application assembly.

21. The brace hinge of claim 20 wherein the adjustment members comprise external threads that cooperate with internal threads of the anterior and posterior apertures to define a position of the adjustment members with respect to the hinge plates.

22. The brace hinge of claim 20, wherein manipulation of the adjustment members further enables adjustment of an orientation of the force application assembly with respect to the first hinge plate.

23. The brace hinge of claim 20, further comprising a second hinge plate.

24. The brace hinge of claim 23, wherein the first and second hinge plates each include a proximal aperture and a distal aperture.

25. The brace hinge of claim 20, further comprising a proximal arm and a distal arm pivotably secured between the first and second hinge plates.

26. The brace hinge of claim 25, wherein rivets secure the proximal and distal arms between the first and second hinge plates.

27. The brace hinge of claim 25, further comprising a first spacer separating the first hinge plate from the proximal arm and distal arm.

28. The brace hinge of claim 27, further comprising a second spacer separating the second hinge plate from the proximal arm and distal arm.

29. The brace hinge of claim 25, further comprising an extension limit attached to the second hinge plate and defining a maximum extension angle of the proximal arm and distal arm.

30. The brace hinge of claim 25, further comprising a flexion limit attached to the second hinge plate and defining a maximum flexion angle of the proximal arm and distal arm.

31. The brace hinge of claim 20, wherein the force application assembly comprises a rigid loading plate.

32. The brace hinge of claim 31, wherein the loading plate is secured to the first ends of the adjustment members.

33. The brace hinge of claim 31, wherein the force application assembly further comprises a semi-rigid member secured to the loading plate.

34. The brace hinge of claim 33, wherein the force application assembly further comprises a resilient pad secured to the semi-rigid member.

* * * * *